(12) United States Patent
Li et al.

(10) Patent No.: US 10,400,265 B2
(45) Date of Patent: Sep. 3, 2019

(54) GEL EXTRACTION DEVICE AND METHODS TO RECOVER BIOMOLECULES FROM AGAR AND AGAROSE GELS

(71) Applicant: The Regents of the University of California, Oakland, CA (US)

(72) Inventors: Rui Li, Riverside, CA (US); Peggy A. Mauk, Riverside, CA (US); Carol J. Lovatt, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 648 days.

(21) Appl. No.: 15/002,386

(22) Filed: Jan. 20, 2016

(65) Prior Publication Data
US 2016/0208314 A1    Jul. 21, 2016

Related U.S. Application Data

(60) Provisional application No. 62/125,302, filed on Jan. 20, 2015.

(51) Int. Cl.
*G01N 1/08*    (2006.01)
*C12Q 1/6806*  (2018.01)

(52) U.S. Cl.
CPC .............. *C12Q 1/6806* (2013.01); *G01N 1/08* (2013.01)

(58) Field of Classification Search
CPC ... C12Q 1/6806; C12Q 2527/101; G01N 1/08
See application file for complete search history.

(56) References Cited

U.S. PATENT DOCUMENTS

| | | | | |
|---|---|---|---|---|
| 6,565,728 B1* | 5/2003 | Kozulic | ............... | B26D 7/1818 |
| | | | | 204/613 |
| 2005/0281709 A1* | 12/2005 | Caldwell | .............. | B26D 7/1818 |
| | | | | 204/613 |
| 2013/0018411 A1* | 1/2013 | Collings | .............. | A61B 17/285 |
| | | | | 606/205 |

* cited by examiner

*Primary Examiner* — David A Reifsnyder
(74) *Attorney, Agent, or Firm* — Gavrilovich, Dodd & Lindsey LLP

(57) ABSTRACT

The disclosure provides for a gel extraction device comprising multifunctional and reusable forceps, a removable cutting element, and a sampler component. The disclosure further provides for a freeze/thaw method which can be used to recover biomolecules from agar or agarose gels.

10 Claims, 12 Drawing Sheets

GEL EXTRACTION DEVICE AND METHODS TO RECOVER BIOMOLECULES FROM AGAR AND AGAROSE GELS

CROSS REFERENCE TO RELATED APPLICATIONS

This application claims priority under 35 U.S.C. § 119 from Provisional Application Ser. No. 62/125,302, filed Jan. 20, 2015, the disclosure of which is incorporated herein by reference in its entirety.

TECHNICAL FIELD

The disclosure provides for a gel extraction device comprising multifunctional and reusable forceps, a removable cutting element, and a sampler component. The disclosure further provides for a freeze/thaw method which can be used to recover biomolecules from agar or agarose gels.

BACKGROUND

A great effort has been made to structurally characterize agar and agarose in view of the ubiquitous use in molecular biology, microbiology and biotechnology. Studies had revealed that agar is formed by a mixture of at least two fractions, agarose and agaropectin. Agarose, the predominant component of agar, is a linear polymer. It is a disaccharide made up of D-galactose and 3, 6-anhydro-L-galactopyranose. Agaropectin is a heterogeneous mixture of smaller molecules that occur in lesser amounts, and is made up of alternating units of D-galactose and L-galactose heavily modified with acidic side-groups, such as sulfate and pyruvate. Agar exhibits hysteresis, melting at 85° C. (358 K, 185° F.) and solidifying from 32-40° C. (305-313 K, 90-104° F.). This property lends a suitable balance between easy melting and good gel stability at relatively high temperatures. Since many scientific applications require incubation at temperatures close to human body temperature (37° C.), agar is more appropriate than other solidifying agents that melt at this temperature, such as gelatin.

SUMMARY

The disclosure provides for an innovative gel extraction device that can be used to slice and transfer target gel slices from agar and agarose. The gel extraction device of the disclosure has additional uses including but not limited to, tissue cutting and transferring, fungi, bacteria, cell and tissue inoculation etc. In a particular embodiment, the gel extraction device disclosed herein comprises multiple function forceps and a sampler in another embodiment the gel extraction device of the disclosure further comprises a cutting element which comprises double-edged sword. The gel extraction device of the disclosure can slice and transfer a desired gel target precisely, efficiently, and also eco-friendly, compared to the traditional razor blade based methods, and other commercial available gel cutting tools.

The disclosure further provides a simple and efficient method to extract DNA, RNA, Protein and other bio-extracts from agar, agarose by using the specific physical property of water, agar, agarose and possible other natural polymers. The method is based on the unique physical property of water, agar and agarose. Temperature lower than −4° C. is first proposed as freezing temperature for agar and agarose, in addition to the existing melting temperature and gelling temperature. Under the freezing temperature, the frozen water (buffer) increased the volume by 9%, this increase in volume enlarges the pore size of agar and agarose. The enlarged pore size was not recoverable when water (buffer) is thawed, therefore, the DNA, RNA, protein or other Bio-extracts released with the thawed buffer by gentle force to the gel slice. By this simple freeze and thaw process, DNA, RNA, protein or other Bio-extracts in the agar or agarose gel can be recovered easily. This method yields high quantity of reasonable quality DNA. In contrast to other methods, there is no laborious steps such as weighing the gel, diluting buffers, having to perform incubation and centrifugation steps, washing steps, and follow specific elution procedures. Moreover, the freeze/thaw methods disclosed herein to not require the use of expensive columns and reagents. Accordingly, the freeze/thaw methods of the disclosure are very eco-friendly, economic and time efficient at almost zero cost with little to no waste produced. The DNA recovered by this method can be used directly for sequencing, PCR and QPCR, and ligation, and transformation are also possible.

In a particular embodiment, the freeze/thaw methods disclosed herein comprise cutting out the interested agar or agarose gel band after gel electrophoresis or culture using the invented forceps described herein. In another embodiment, the method provides for placing the gel slice into a micro-centrifuge tube with a corrugated structure on the inner wall (e.g., see FIG. 11) or any other suitable tube. In yet another embodiment, the method calls for freezing the gel slice by using a freezing means. Examples of freezing means includes freezing the gel slice by placing the tube with the gel slice in liquid nitrogen (−196° C.); freezing the gel slice by placing the tube with the gel slice in a −80° C. freezer until the gel frozen; freezing the gel slice by placing the tube with the gel slice in a −4 to −20° C. freezer until the gel slice is frozen. It should be noted that the frozen gel slice can be used immediately or stored indefinitely at a temperate of −4° C. or lower. In a further embodiment, the method then calls for thawing the gel slice rapidly by providing a heating means. Examples of heating means, includes hand warming, placing the tube in a heated bath or heating block, or using a blow dryer. In yet a further embodiment, the method calls for expelling liquid from the gel slice using a forcing means. Examples of a forcing means, includes pressing gel slice gently against the wall of the micro-centrifuge tube with a pipette tip, toothpick, or similar object, or waving the tube in the air, or by centrifugation. In another embodiment, the method provides for extracting and storing the liquid expelled from the gel, wherein the gel comprises the targeted agent to be recovered (e.g., protein, polynucleotide, etc.). The method of the disclosure requires little effort, minimal cost in comparison to similar gel extraction methods, does not require the use of buffer or columns for melting agarose, no washing steps, or use of any biohazardous agents. Thus, the method disclosed herein, is very economically and environmentally friendly. Moreover, the freeze/thaw methods disclosed herein are suitable for extracting various biomolecules from agarose after gel electrophoresis, and for extracting metabolites produced from cultures grown on/in agar.

In a particular embodiment, the disclosure provides for a gel extraction device comprising: a multifunctional and reusable forceps, a cutting element that can be detachably attached to the forceps, wherein the cutting element is used to cut a slice of gel from an agar or agarose gel; and a sampler component that can be detachably attached to the forceps, wherein the sampler component in conjunction with the forceps is used to collect the gel slice. In another embodiment, the forceps comprises: a left and right housing that can be joined together by using fastening means, wherein the left and right housing comprises an elongated arm portion connected to a rectangular shaped portion, wherein the rectangular shaped portion comprises a longitudinal groove that can accommodate a spring and a retractable rod assembly. In a further embodiment, the rectangular shaped portion of the left and right housing further comprises various holes that can used with the fastening means to join the left and right housing together, and a hole that can accommodate a shaft or pin. In yet a further embodiment, the ends of each of the elongated arm portion of the left and right housing comprises projections that are dimensioned so as to fit into holes on the sampler. In another embodiment, the forceps comprises a spring located within the longitudinal groove, wherein the spring comprises a plurality of hooks; a retractable rod assembly comprising a spring action projection, a loop that is attached to a hook of spring, and a deformable rectangular plate that can be used to engage and disengage the spring when the spring action projection is pressed, wherein the rod can be extended by manually sliding the spring action projection forward, and wherein the rod can be retracted by using the tension of the spring by pressing down on the spring action projection; and optionally, a small projection near the end of the plate that is attached to the spring that can fit into a small groove of the forceps housing to provide additional stability to the rod assembly. In a certain embodiment, the disclosure provides for a gel extraction device comprising: a multifunctional and reusable forceps, a cutting element that can be detachably attached to the forceps, wherein the cutting element is used to cut a slice of gel from an agar or agarose gel and wherein the cutting element is detachably attached to the end of the retractable rod assembly that can be detached from the forceps when the rod is retracted by pressing down on the spring action projection; and a sampler component that can be detachably attached to the forceps, wherein the sampler component in conjunction with the forceps is used to collect the gel slice. In another embodiment, the cutting element comprises an opening that is slideably attachable to the end of rod assembly; a housing which comprises a double edged sword, wherein the housing comprises an angular bend of greater than 90 degrees but less than 150 degrees in the middle portion of the housing; and optionally a flat plate located at the opposite end of the cutting element. In a particular embodiment, the disclosure also provides for a gel extraction device comprising: a multifunctional and reusable forceps, a cutting element that can be detachably attached to the forceps, wherein the cutting element is used to cut a slice of gel from an agar or agarose gel; and a sampler component that can be detachably attached to the forceps, wherein the sampler component in conjunction with the forceps is used to collect the gel slice, and wherein the sampler comprises a left and right housing that can be slideably attached to each other and which comprise receptacles that can accommodate the ends of the arms of the forceps. In a further embodiment, the right housing has three panels, a left and right panel of equal dimensions that comprises a groove at the bottom of the panels, and a back panel which is shorter than the left and right panel so that there is a slotted opening at the base of the back panel; and wherein the left housing has a bottom panel that is dimensioned to fit within the slotted opening of the back panel and wherein the lateral sides of the bottom panel can slideably insert into the grooves of the left and right panels. In a certain embodiment, the disclosure also provides for the gel extraction device disclosed herein, that the forceps is made of stainless steel; and wherein the cutting element and sampler component are made of stainless steel, plastic, or combination thereof. In a further embodiment, the disclosure further provides that the forceps is reusable while the cutting element and/or sampler component are disposable. In an alternate embodiment, the disclosure provides that the forceps, cutting element, and the sampler component are all reusable.

In a certain embodiment, the disclosure provides, a freeze/thaw method to recover biomolecules from an agarose or agar gel comprising: freezing a slice of agar or agarose gel comprising a biomolecule placed in a micro-centrifuge tube freezing a slice of agar or agarose gel comprising a biomolecule that has been placed in a micro-centrifuge tube using a freezing means; thawing the gel slice using a heating means; expelling liquid comprising the biomolecule from the gel slice by using a forcing means; collecting the liquid comprising the biomolecule. In one embodiment, the biomolecule is a polynucleotide. In an alternate embodiment, the biomolecule is selected from protein, amino acids, metabolites and bio-extracts in another embodiment, the gel is an agar gel. In a further embodiment, the micro-centrifuge tube comprises inner corrugated walls and wherein the forcing means comprises a pipette that has corrugated outer walls which is used to press the gel slice against the walls of the micro-centrifuge tube.

In a particular embodiment, the disclosure also provides a freeze/thaw method to recover biomolecules from an agarose or agar gel comprising: extracting a slice of agar or gel comprising a biomolecule using the gel extraction device of the disclosure; freezing the slice of agar or agarose gel at a temperature of 4° C. or lower; thawing the gel slice using a heating means; expelling liquid comprising the biomolecule from the gel slice by using a forcing means; collecting the liquid comprising the biomolecule.

The details of one or more embodiments of the disclosure are set forth in the accompanying drawings and the description below. Other features, objects, and advantages of the disclosure will be apparent from the description and drawings, and from the claims.

DETAILED DESCRIPTION

Figure 1:
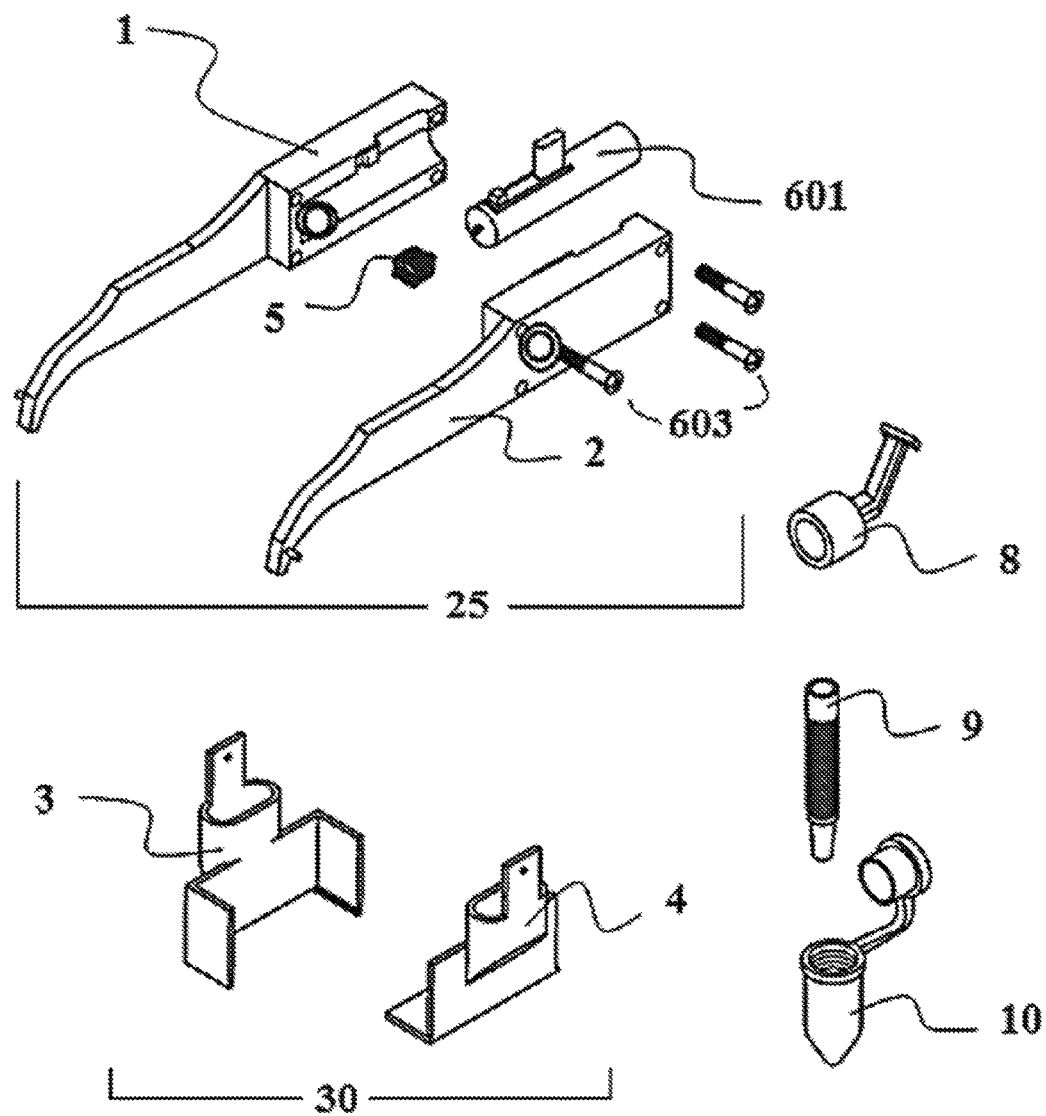
FIG. 1 provides an exploded view of various components making up the gel extraction device of the disclosure and various, other components that can be used with the gel extraction device and/or with the freeze/thaw methods of the disclosure.

Unless specifically noted otherwise herein, the definitions of the terms used are standard definitions used in the art of pharmaceutical sciences. As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Also, the use of "or" means "and/or" unless stated otherwise. Similarly, "comprise," "comprises," "comprising," "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the are to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies presented therein.

Provided herein are exemplary embodiments for making and using the gel extraction device and associated components, and the freeze/thaw methods of the disclosure. However, it should be understood that additional embodiments are fully contemplated, based upon the larger disclosure and context provided by the specification and figures presented herein. Accordingly, the exemplary embodiments presented herein should not be construed as providing the only basis for claimed subject matter. Instead, the claimed subject matter should be looked at as finding adequate and reasonable support in view of the specification and figures presented herein in their entirety, which would also include any well-known teachings in the art at the time the application was filed.

Referring to the drawing figures, use of reference numerals has been provided in order to allow for identification of various structural features, including use of the same reference numerals for identifying said structural feature in the various views of the device.

It has been reported that more than 21,000,000 samples of DNA are gel extracted for use in cloning. Usually, the target band is excised using a sterile razor blade and then the interested molecules extracted by various techniques. These techniques include dialysis tubing method, spin-column method, paper strip method and other methods such as electroelution, "freeze and squeeze" method, and Gelase treatment. All these methods require multiple processing steps, are generally time consuming and require equipment such as fine balances, water baths, centrifuges, buffers, pipetting, and etc. The more recent techniques, use steps that require agarose to melted with melting agents, and use of spin columns. Agarose, however, contains various impurities which may inhibit downstream reactions if not efficiently removed from the DNA, which is a possibly drawback to using the column methods described above. The method of choice depends on the requirement on the purity and the condition of the laboratory.

The disclosure provides for a gel extraction device that can be used to cut and transfer gel slices comprising target molecules (e.g., proteins, polynucleotides, etc.) from an electrophoresed gel, or can be used to cut and transfer cell, tissue, callus, bacteria or fungal cultures from agar. Each of the components making up the gel extraction device provide advantages in comparison to similar devices. For example, most devices for gel extraction suffer from the all too common problem of losing the gel slice while trying to transfer the cut slice from the gel to a container. By contrast the device of the disclosure has a sampler component that protects the gel slice from inadvertent. 'drops.' Furthermore, the devices, disclosed herein can be used in many fields beyond molecular biology, for example, the Sampler can be used not only to transfer the target gel, but also to transfer the cultured material from the old medium to a new one, to take samples from agar culture medium to measure nutrient consumed or metabolites produced by cultured living organism. Components making up the gel extraction device are either disposable e.g. the double-edged cutting device, pipet tips and micro-centrifuge tubes or reusable, such as the forceps and the Samplers. The gel extraction device is dimensioned such that it can be easily manipulated using one hand. Moreover, the device can be manipulated in a similar manner as common forceps, whereby the arms of the multifunctional forceps disclosed herein can be manipulated by applying pressure on the arms to press the tips of the arms together or alternatively to spread the tips apart. Therefore, manipulating the arms of the forceps allows for manipulation of the sampler component to open and close. Accordingly, the sampler component can function like a spatula where the sampler can be used scoop up a gel slice and hold it securely with the closed sampler component.

The gel extraction device of the disclosure can be comprised of one or more structural features depicted in FIGS. 1-11.

FIG. 1 presents an exploded view of forceps 25, sampler 30, cutting element 8, extractor 9 and collector 10 that used for gel or sample cutting and components used for transferring target molecules recovered from the cut agar or/and agarose gel. Forceps 25 is comprised of a right forceps housing 1 and left forceps housing 2, spring 5, and rod 601. Right forceps housing 1 and left forceps housing 2 can be attached to each other using a fastening means. Examples of fastening means, include, but are not limited to, using fasteners (e.g., screws, clips, rivets and the like); using fastening agents (e.g., glues, cements and the like); or welding. In one embodiment, the fastening means is screws 603. Sampler 30 is comprised of right sampler housing 3 and left sampler housing 4. Other structures depicted in FIG. 1, include gel cutting element 8, extractor 9 and collector 10.

Figure 2A:
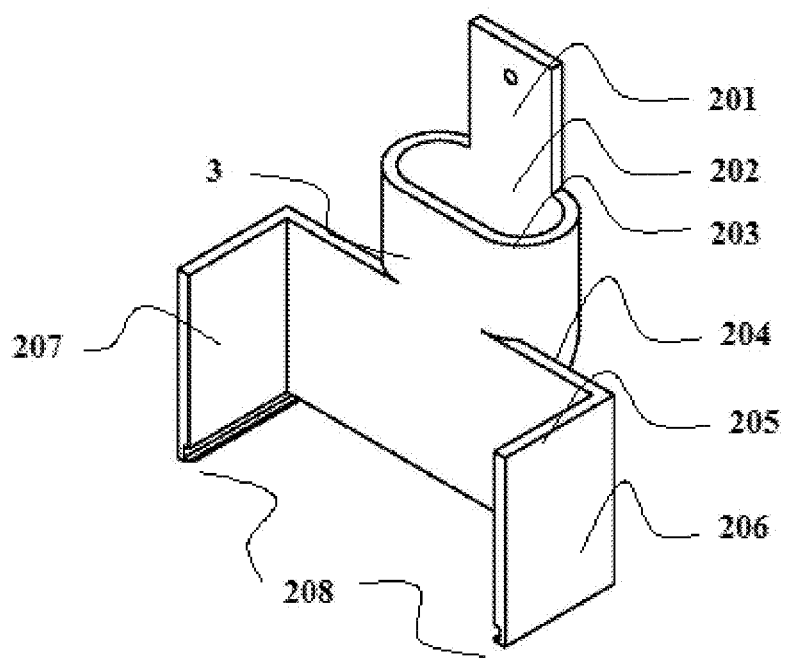
FIG. 2A-B provides various views of components making up the Sampler element of the gel extraction device. (A) Provides a close-up view of the right sampler housing; while (B) provides a cut away detailed view of the back and left panel of the right sampler housing. The detailed structure of the Sampler.

FIG. 2A presents a close-up view of right sampler housing 3. Hole 201 is dimensioned to receive a small projection 604 from left forceps housing 2 or right forceps housing 1 (e.g., see small projections 604 in FIG. 6.) In particular embodiments, hole 201 is round or oval in shape. In other embodiments, hole 201 is rectangular, square, hexagonal, triangular, or uniquely shaped. Security belt 202 with hole 201 provides an alternative way to secure right sampler housing 3 with left forceps housing 2 or right forceps housing 1. Main joint receptacle 203 of main joint housing 204 is suitably dimensioned to receive a bottom end 605 of forceps 25. Right sampler housing 3 further comprises a lower portion comprised of three panels, right panel 206 and the left panel 207 and the back panel 205. All three panels have same height at the top. The bottom of back panel 205 is shorter than adjoining right panel 206 and the left panel 207, thereby providing a slotted opening which allows bottom panel 305 of left sampler housing 4 in FIG. 3 to slidably pass through back panel 205 according to the gel slice or sample size. Both the right panel 206 and the left panel 207 have an inset groove 208 at the bottom of the panels to receive bottom panel 305 of left sampler housing 4. Inset groove 208 slidably orients the connection of bottom panel 305 of left sampler housing 4 to right sample housing 3 and further prevents any possible dislocation of the bottom panel 305 from left sampler housing 3 during sample collection.

FIG. 23 presents a cut away detailed view of the back panel 205 and the left panel 207 of right sample housing 3 of Sampler 30. As shown, the bottom of back panel 205 is shorter than adjoining left panel 207, thereby providing a slotted opening which allows bottom panel 305 of left sampler housing 4 to slidably pass through back panel 205. Also shown, is a close-up of an inset groove 208 at the bottom of the left panel 207 that is dimensioned to receive the side portion of bottom panel 305 of left sampler housing 4.

Figure 3:
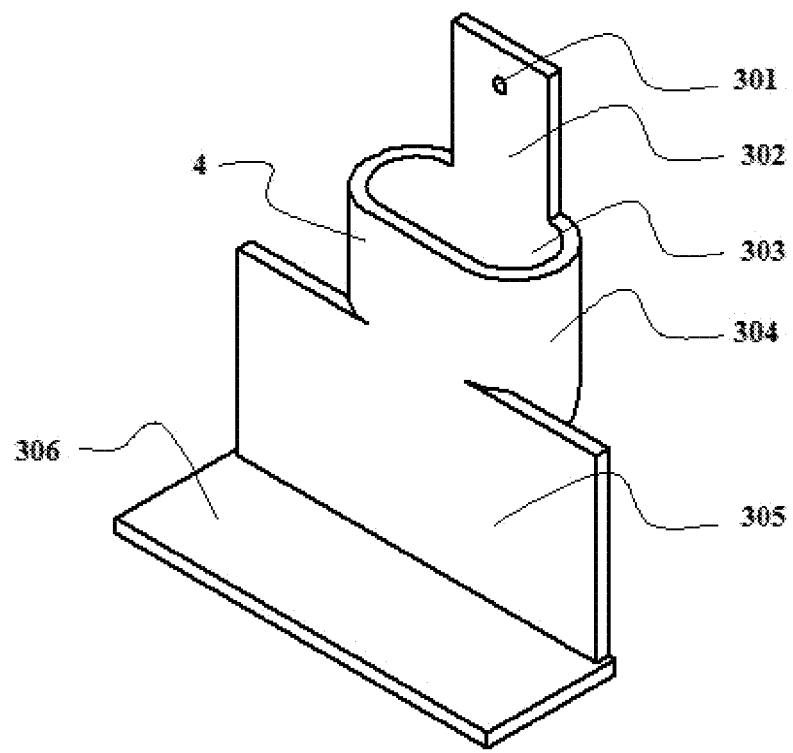
FIG. 3 provides a close-up view of the left sampler housing of the Sampler.

FIG. 3 provides a close-up view of the structure of left sampler housing 4 of Sampler 30. Hole 301 is dimensioned to receive a small projection 604 from left forceps housing 2 or right forceps housing 1 (e.g., see small projections 604 in FIG. 6.) In particular embodiments, hole 301 is round or oval in shape in other embodiments, hole 301 is rectangular, square, hexagonal, triangular, or uniquely shaped. Security belt 302 with hole 301 provides an alternative way to secure right sampler housing 3 with left forceps housing 2 or right forceps housing 1. Main joint receptacle 303 of main joint housing 304 is suitably dimensioned to receive a bottom end 605 of forceps 25. Left sampler housing 4 further comprises a lower portion comprised of two panels, back panel 305 and bottom panel 306. Back panel 305 is narrower in width than the bottom panel 306, which allows the bottom panel 306 of left sampler housing 4 to slidably insert into inset grooves 208 of right panel 206 and left panel 207 of right sampler housing 3. Possible dislocation of the bottom panel 306 and target gel or sample from damage is prevented by fit between bottom panel 306 and the groove at the bottom of back panel 205 of right sampler housing 3.

Figure 4A:
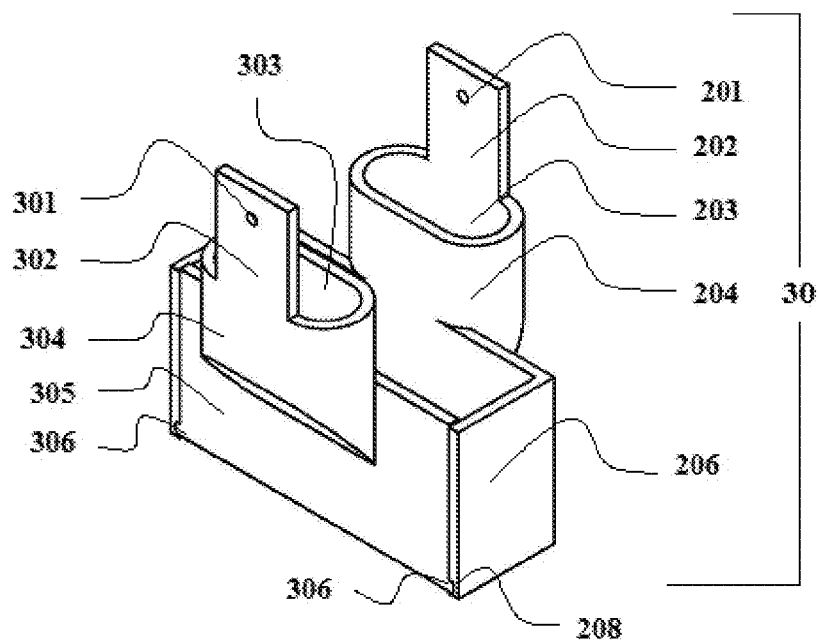
FIG. 4A-B provides various views and perspectives of components making up the Sampler element of the gel extraction device. (A) Provides a top front perspective of the right sampler housing joined with the left sampler housing; while (B) provides a partial enlarged view of the tight junction between the housing components of the Sampler.

FIG. 4A provides a top front perspective view of left sampler housing 4 and right sampler housing 3 of sampler 30. Hole 201 and hole 301 are dimensioned to receive a small projection 604 from left forceps housing 2 and right forceps housing 1 to hold both left sampler housing 4 and right sampler housing 3 of sampler 30 with forceps 25. Security belt 202 and security belt 302 comprising hole 201 and hole 301 are an alternative way to secure both left sampler housing 4 and right sampler housing 3 of sampler 30 with forceps 25. The grooves of the main joint receptacle 203 and main joint receptacle 303 of main joint housing 204 and main joint housing 304, respectively, are dimensioned so as to receive the bottom ends 605 of forceps 25. Also shown, is right panel 206 comprising inset groove 208 of the right sampler housing 3, back panel 305 of the left sampler housing 4. The sides of the bottom panel 306 of left sampler housing 4 are held by the inset grooves 208.

Figure 4B:
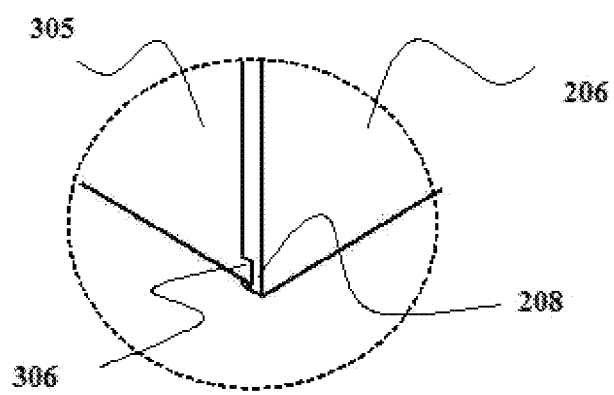

FIG. 4B provides a partial enlarged view to show a side of the bottom panel 306 of left sampler housing 3 slideably inserted in an inset groove 208 of right panel 206 of right sampler housing 3. As shown, back panel 305 of the left housing 4 is tightly joins with the right panel 206 of the right sampler housing 3 of the sampler 30.

Figure 5:
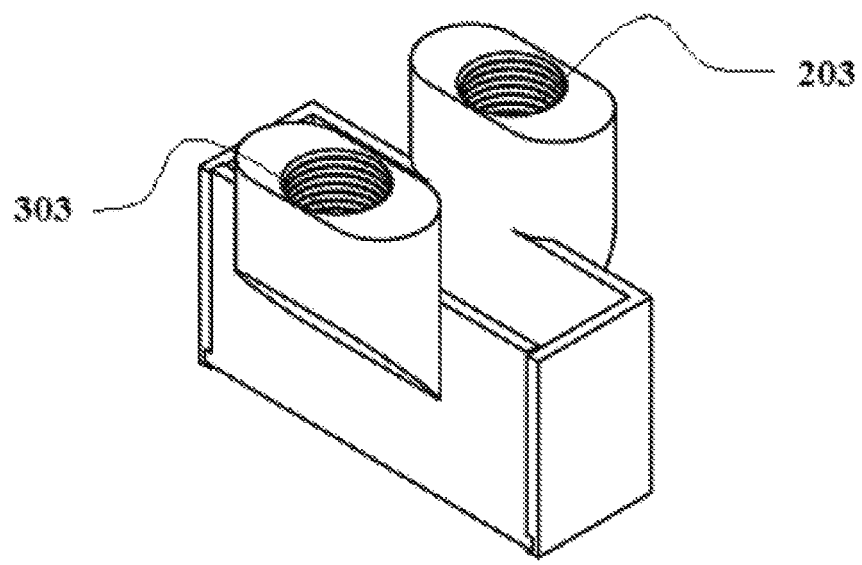
FIG. 5 provides a top from perspective of an alternate embodiment of the Sampler where forceps have threaded bottom ends.

FIG. 5 provides a top front perspective view of the sampler 30 showing an alternative way for the forceps 25 to join with the sampler 30 via threads. Female threads 501 and 502 join with the threated bottom end 605 (not shown).

Figure 2B:
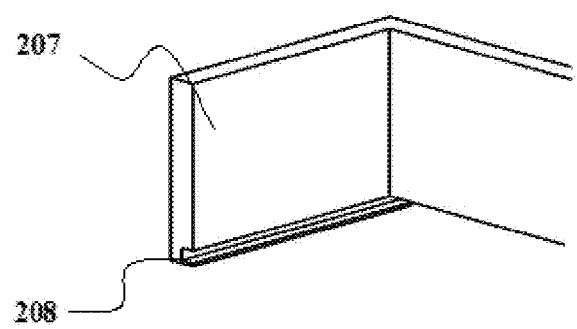
Figure 6:
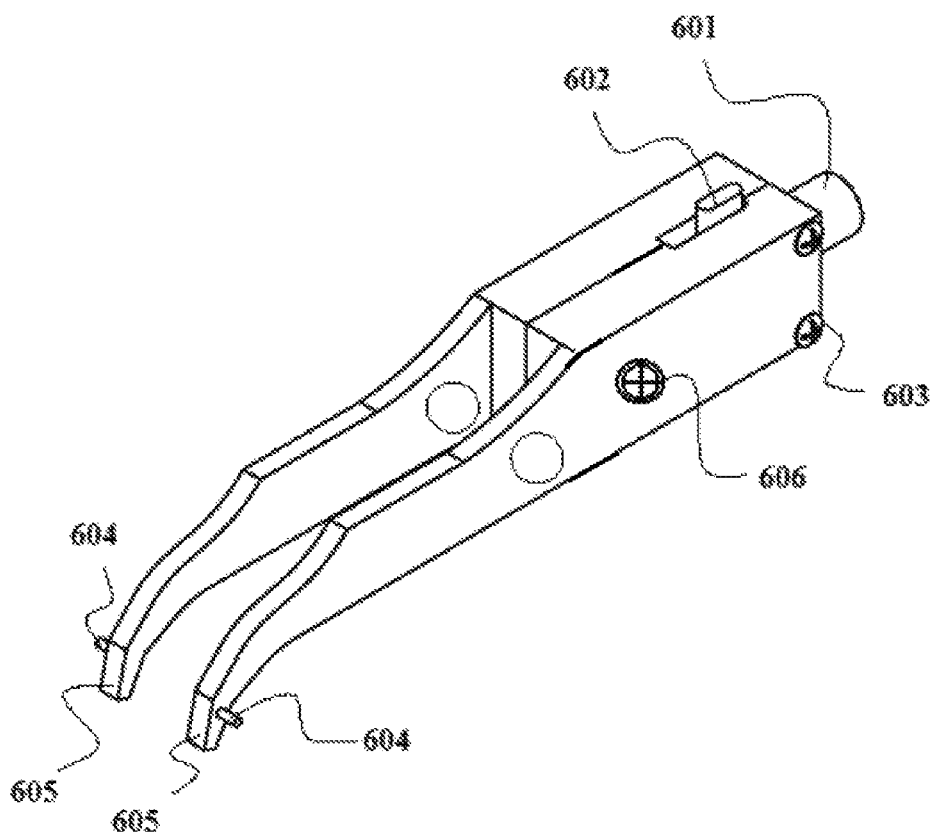
FIG. 6 provides a top front perspective of the multifunctional and reusable forceps making up the gel extraction device of the disclosure.

FIG. 6 provides a top front perspective view of the forceps 25. Forceps 25 comprises left forceps housing 2 and right forceps housing 1 which can be joined together by a fastening means, e.g., screws 603 and pin 606. Rod 601 is at the top end of the forceps 25 and can be stretched out manually by pushing forward protrusion 602 and backward automatically when pushing down the protrusion 602. Rod 601 when extended is used to join with gel cutting device 8 as showed in FIG. 1 and FIG. 8. Small projections 604 are used to match with holes 201 and 301 as showed in FIGS. 2 and 3. Bottom ends 605 of forceps 25 are used to insert into the main joint receptacles. 203 and 303 as shown in FIG. 2, FIG. 3, and FIG. 5. The shape or structure of the bottom ends 605 of the forceps can be vary according to the main joint holder receptacles 203 and 303.

Figure 7:
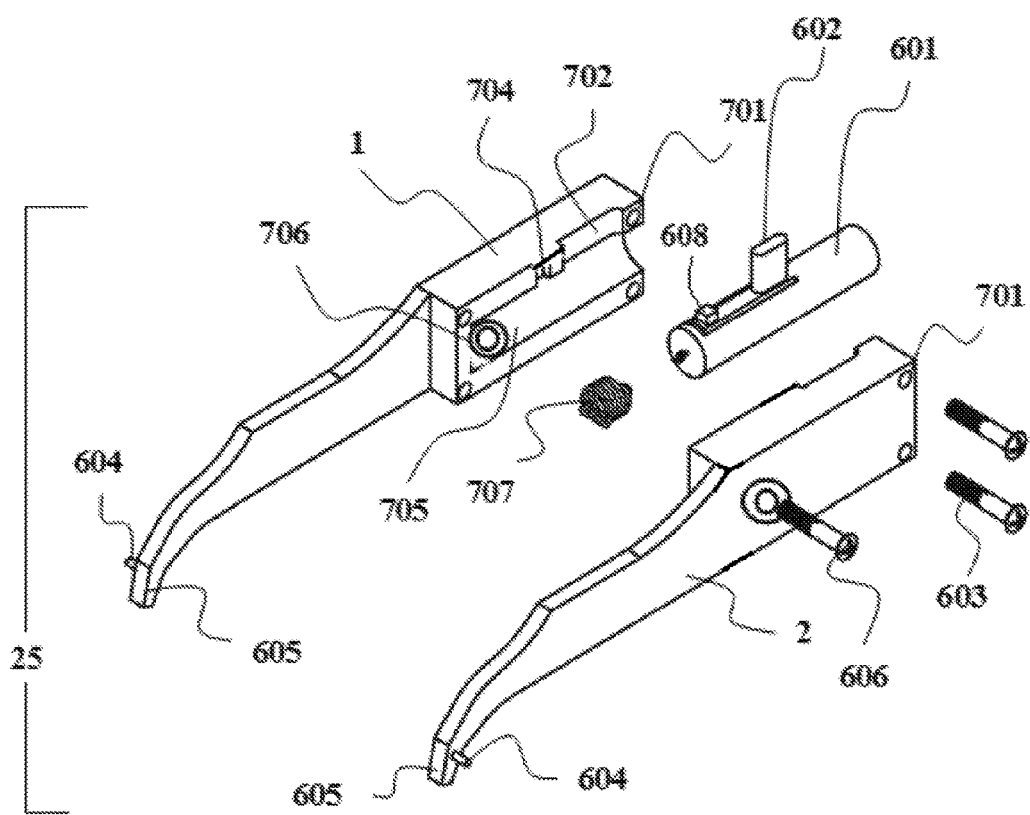
FIG. 7 provides an exploded view of the various structural components making up the multifunctional and reusable forceps.

FIG. 7 provides an exploded view of forceps 25. Forceps 25 is comprised of right forceps housing 1, left forceps housing 2, spring 707, and rod 601. Right forceps housing 1 and left forceps housing 2 can be joined together using a fastening means, e.g., screws 603. For example, screws 603 can attach right forceps housing 1 and left forceps housing 2 together by using internal threads 701. Each of right forceps housing 1 and left forceps housing 2 has a longitudinal groove 705 that is each dimensioned to fit a radius of the rod 601 and half portion of spring 707. Rod 601 can be extended by pushing down on spring loaded protrusion 602 and retracted by sliding back spring loaded protrusion 602. Slide groove 702 allows protrusion 602 to slide backwards and/or forwards as needed. Rod 601 and spring 707 are held inside of longitudinal groove 705. Spring 707 comprises two hooks, hook 721 and hook 722, on each end used to hook up with the hoop on the end rod 601 and pin 606. A half way groove 704 can accommodate small protrusion 608. Small protrusion 711 can provide additional support for rod 601 when rod 601 is elongated. Each of small protrusions 604 on each part of the forceps 25 is used to match with hole 201 and hole 301 as showed in FIG. 2 and FIG. 3. Each of bottom ends 605 of forceps 25 is used to insert into the main joint receptacle 203 and main joint receptacle 303 as showed in FIG. 2 and FIG. 3. The shape or structure of the bottom ends 605 of the forceps can be vary as long as the ends fit main joint receptacle 203 and main joint receptacle 303 in FIG. 2, FIG. 3 and FIG. 5.

Figure 8A:
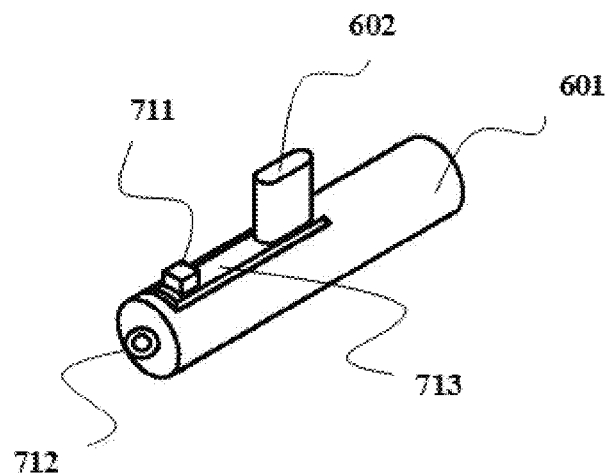
FIG. 8A-B provides various views of components making up the forceps. (A) provides a detailed view of the rod and groove components of the forceps. (B) provides enlarged view of the spring and hook assembly of the forceps.

FIG. 8A provides a detailed view of the rod 601. Rod 601 comprises spring loaded protrusion 602 and small protrusion 711. Both spring loaded protrusions 602 and small protrusion 711 are located on a rectangle plate 713. Rectangle plate 713 is connected with rod 601 at the front end. The rectangle plate 713 has elasticity to allow the plate to be pushed down via spring loaded protrusion 602. Hoop 712 is used to hook spring 707. The pushed out rod 601 is used to join with opening 801 of the gel cutting element 8 as showed in FIG. 9. When spring loaded protrusion 602 is pushed down, the elastic force of spring 707 will pull rod 601 back in groove 705. As result of the rod 601 being pulled back by the elastic force of spring 707, the used gel cutting element 8 is also being pulled off from the rod 601.

Figure 8B:
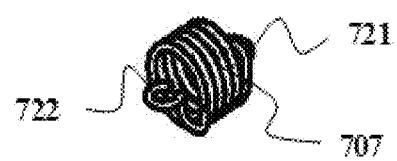

FIG. 8B provides enlarged view of the spring 707 to show hook 721 and hook 722.

Figure 9A:
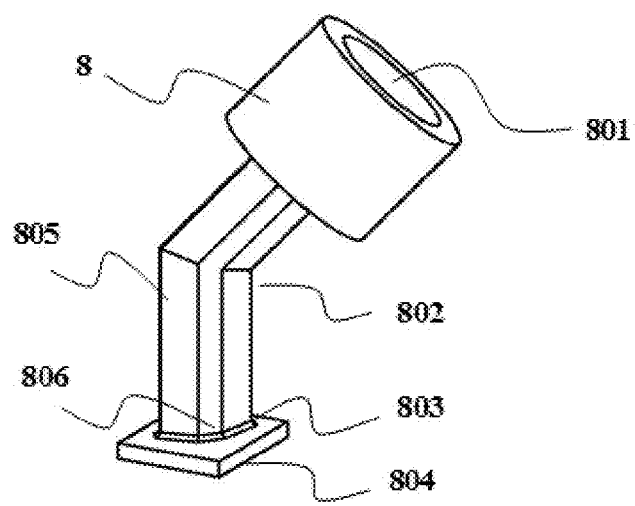
FIG. 9A-B provides various views of a detachable cutting element that can be used with the gel extraction device of the disclosure. (A) Provides a front perspective view of the cutting element; while (B) provides a sectional view of the double edged sword.

FIG. 9A provides a front perspective view of cutting element 8. The to part of cutting element 8 comprises opening 801 which is dimensioned to accommodate rod 601. Cutting element 8 comprises angle 802 in the middle part of the housing, which allows the cutting area to be visible during the operation. In particular embodiment, angle 802 can be angle between 90 degrees to 180 degrees, between 100 degrees to 170 degrees, between 110 to 160 degrees, between 120 to 150 degrees, between 130 to 140 degrees, about 120 degrees, about 130 degrees, or about 135 degrees. The central portion 806 of the cutting element housing is of sufficient thickness in order to support the sword and prevent bending due to the unbalanced force. Flat plate 804 at the bottom of cutting element 8 is an alternative way to keep the cutting to be stable and protect the equipment from damage.

Figure 9B:
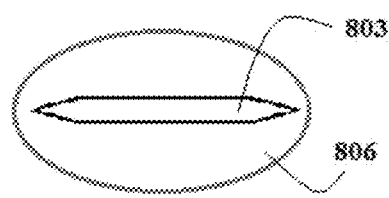

FIG. 9B provides a sectional view of the double-edged sword 803 surrounded by central part 806.

Figure 10:
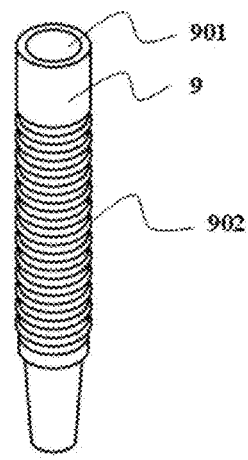
FIG. 10 provides a close-up view of the pipet tip that can be used with the gel extraction device of the disclosure and/or with the freeze/thaw methods of the disclosure.

FIG. 10 presents a front perspective view of a pipet tip with corrugated structure 902 on the outside of the tip wall. Opening 901 is dimensioned to fit standard micropipettes, such as those manufactured by various venders known in the art. In certain embodiments, corrugated structure 902 matches with corrugated structure 1001 showed in FIG. 11. Corrugated structure 902 can be used to gently press against a target gel slice to expel biomolecules placed, e.g., a gel slice placed in micro-centrifuge tube 10.

Figure 11:
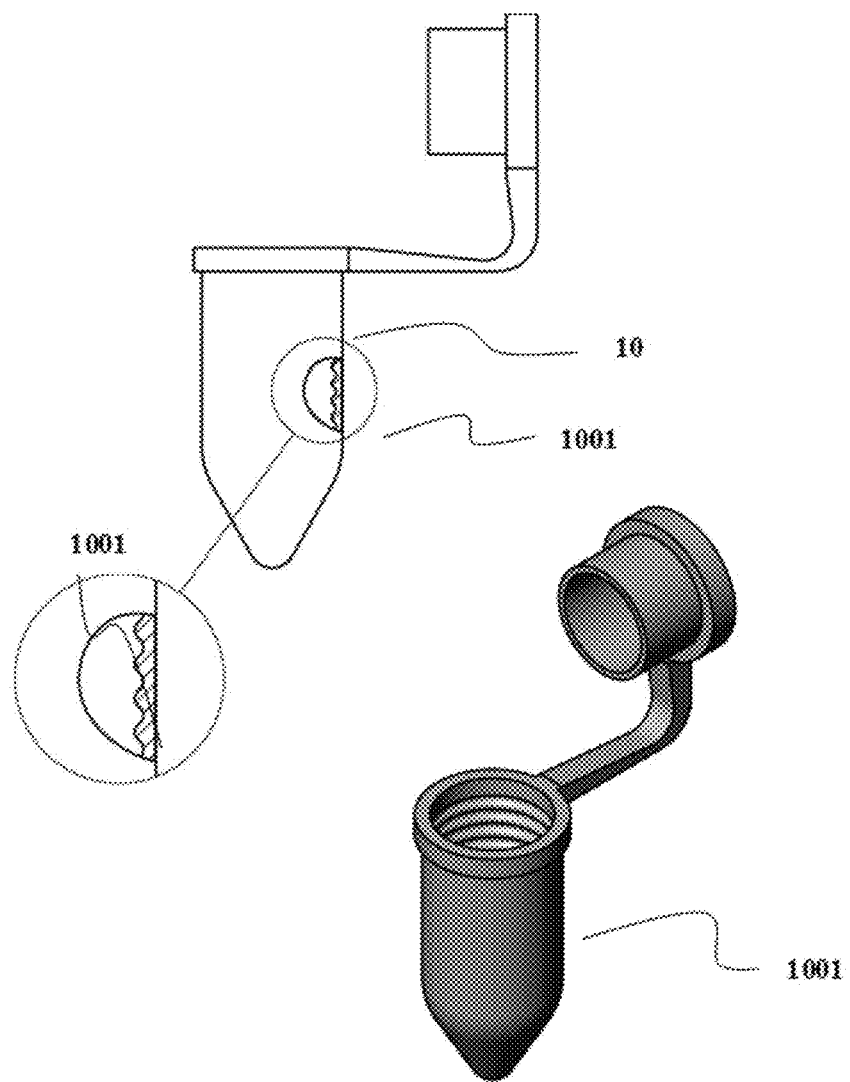
FIG. 11 provides views of micro-centrifuge tube comprising corrugated inner walls that can be used with the gel extraction device of the disclosure and/or with the freeze/thaw methods of the disclosure.

FIG. 11 presents a detailed partial cut away view of the corrugated structure 1001 on the inner wall of the micro-centrifuge tube 10. Micro-centrifuge tube 10 is dimensioned so as to fit standard size holders in micro-centrifuges. Also provided, is three dimensional view of a micro-centrifuge tube 10 with corrugated structure 1001 on the inner wall. The corrugated structure matches with corrugated structure 902 on the outside of the tip 9 to gently press the target gel slice to expel liquid comprising biomolecules.

The disclosure further provides a process for recovering biomolecules from agar or agarose gels using the freeze/thaw methods disclosed herein. It should be understood that the freeze/thaw methods disclosed herein can be performed using the gel extraction device of the disclosure including components that can be used with said device, such as tip 9 and micro-centrifuge tube 10, or alternatively, the freeze/thaw methods can be performed without using said gel extraction device. The freeze/thaw methods disclosed herein are principled on the basis that water molecules expand to about 9% of their volume when water is converted to ice when exposed to freezing to sub-freezing temperatures, and this volume expansion changes the pore or size of gelled agar and agarose. Agar and agarose comprise three-dimensional matrices formed when helical agar and agarose molecules form supercoiled bundles that organize into three-dimensional structures with channels and pores running through the structures. The 3-D structure is held together with hydrogen bonds and can therefore the organized structure can be disrupted by breaking these hydrogen bonds by heating above a certain temperature. During the freezing process of gels comprising agar or agarose, the original pore size or the molecular mesh of the gels expand by about 9% due to the volume expansion from water being converted to ice. The overall structure agar and agarose, however, remains largely unchanged, in that the agar and agarose gels do not fracture even with the volume expansion. However, the original pore size of the agar and agarose gel are irreparably changed by the volume expansion. In particular, the pore size is permanently enlarged, even with the thawing of the gel. The enlarged pore size, however, allows biomolecules that are trapped with the gel to escape when liquid is expelled from the thawed gels. The freeze/thaw methods disclosed herein allow for the recovery of these biomolecules from thawed gels. Any number of biomolecules can be recovered from the thawed gels, including polynucleotides, such as RNA, DNA, cDNA, and smaller fragments of the foregoing; polypeptides, such as proteins; amino acids; metabolites from bacterial, fungal, plant or eukaryotic cell cultures; etc. Accordingly, the freeze/thaw methods disclosed herein can be used to analyze metabolite production, nutrient consumption, etc. from cultures grown on/in agar, such as bacterial, fungal, eukaryotic cell, protoplast and plant tissue cultures.

EXAMPLES

Determining Suitable Temperatures to Freeze Agar and Agarose Gels.

In order to determine which temperature would be suitable for freezing agar and agarose gels, Agar and agarose gels (0.8%-3.5%) were placed at 0° C., −4° C., −20° C., −80° C. and −196° C., respectively. The gels froze at −4° C., −20° C., −80° C. and −196° C., but not at 0° C. The frozen gels when thawed did not disintegrate at room temperature. The buffer contained in the gel slice could be released by gently pressing the gel slice against the wall of a micro-centrifuge tube with a pipette tip. The results demonstrate that as long as the gel is frozen at less than −4° C., the DNA or any other molecules in the buffer were released from the gel once thawed at ambient temperature.

Testing Techniques to Expel Liquid Comprising Target Molecules from Thawed Gel.

When the concentration of agar or agarose is low, e.g., 0.8% of agar or agarose, the buffer with DNA or other molecules are released automatically when the frozen gel is thawed at ambient temperature or at an elevated temperature, such as 37° C. One method to forcibly expel liquid from the gel comprising placing the gel into a 0.6-1.5 mL micro-centrifuge tube, freezing and thawing the gel, and pressing the gel against the inner wall of a micro-centrifuge tube using a pipet tip. The second method was to place the micro-centrifuge tube on a vortex, and shake the tube at the lowest settings for a few seconds. The third method tested was to shake the tube in air by hand. All techniques provided a visible eluent. However, for recovery of DNA from a higher concentration of agarose (3.5%), centrifugation was found to be the best choice.

Testing Whether Freezing the Gels Changed Mesh Size.

Figure 12A:
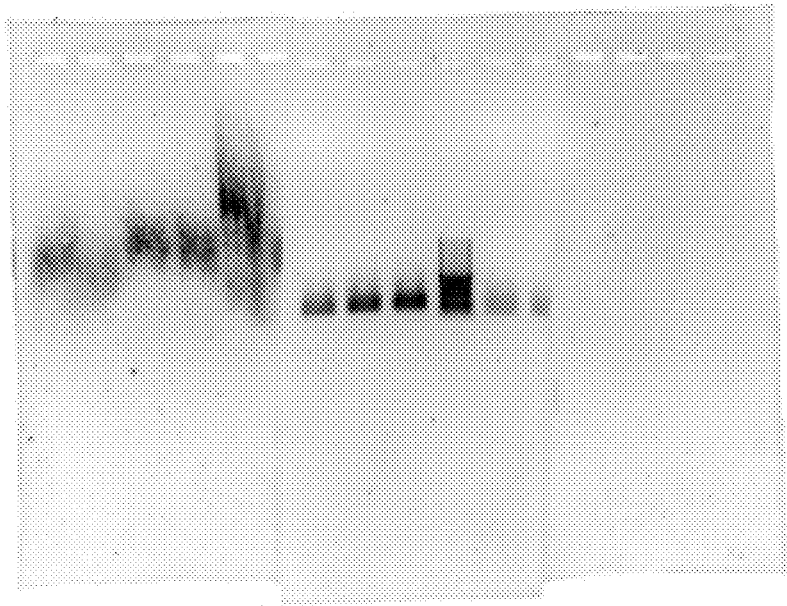
FIGS. 12A-B presents photos of agarose gels that were run with DNA fragments and markers. (A-B) gels (0.8% agarose in TAE buffer) were frozen at −20° C. (left section) or not frozen (middle section and right section) prior to loading. The DNA fragments and markers did not effectively separate by size using the frozen/thawed gel (left section) while the DNA marker and DNA fragment separated by size via the non-frozen gel (middle section) by gel electrophoresis. Unloaded gel control (right section).
Figure 12B:
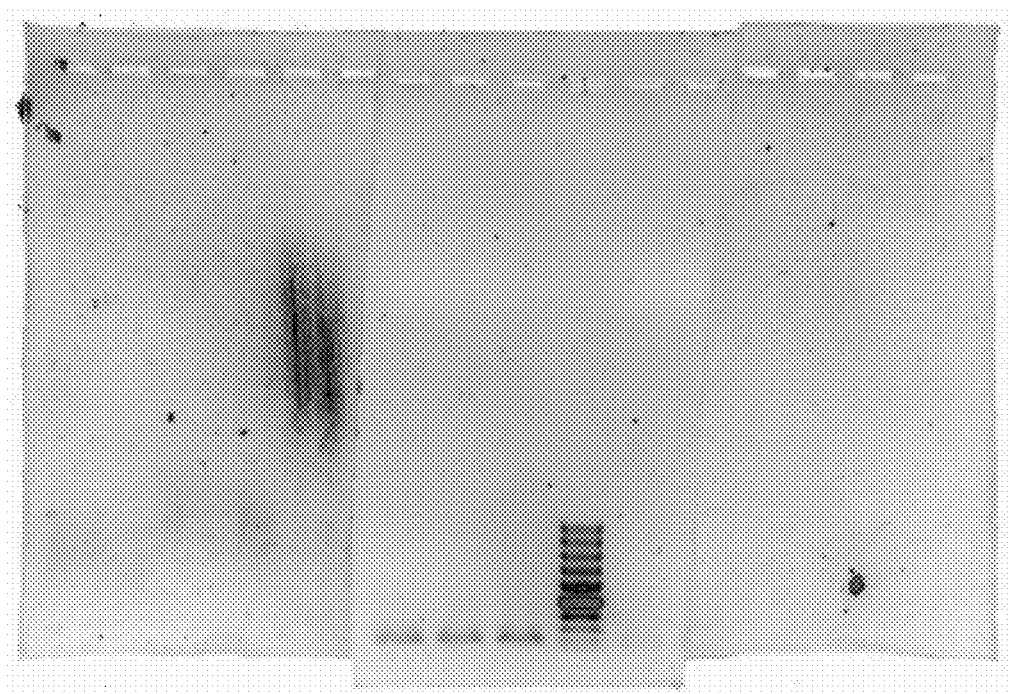
Figure 13:
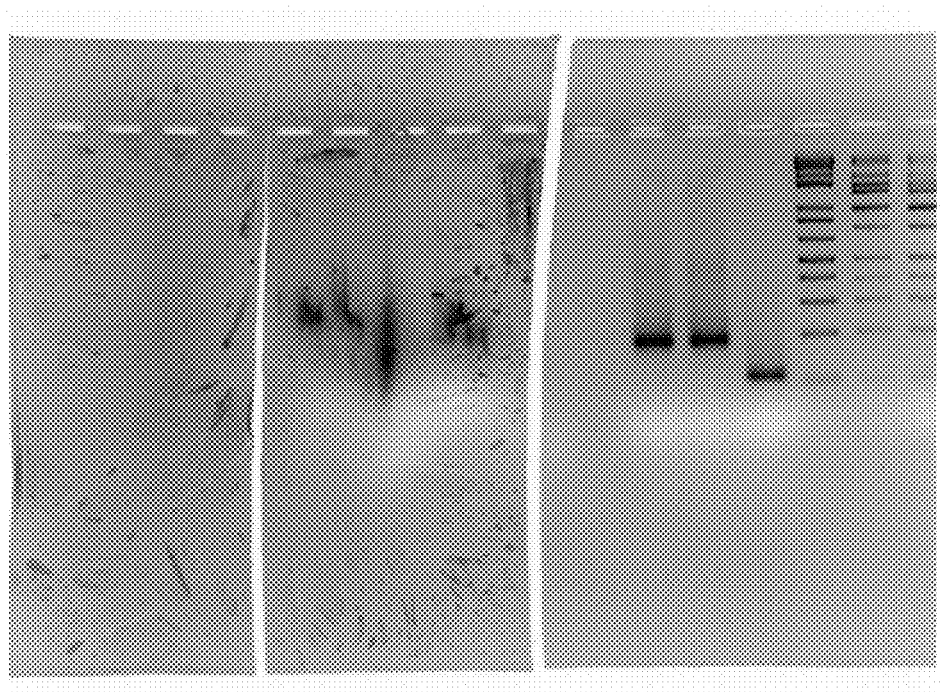
FIG. 13 presents photos of agarose gels that were run with DNA fragments and markers. The gels (3.5% agarose in TAE buffer) were frozen at −20° C. (middle section) or not frozen (left section and right section) prior to loading. The DNA fragments and markers did not effectively separate by size using the frozen/thawed gel (middle section) while the DNA marker and DNA fragment separated by size via the non-frozen gel (right section) by gel electrophoresis. Unloaded gel control (left section).
Figure 14A:
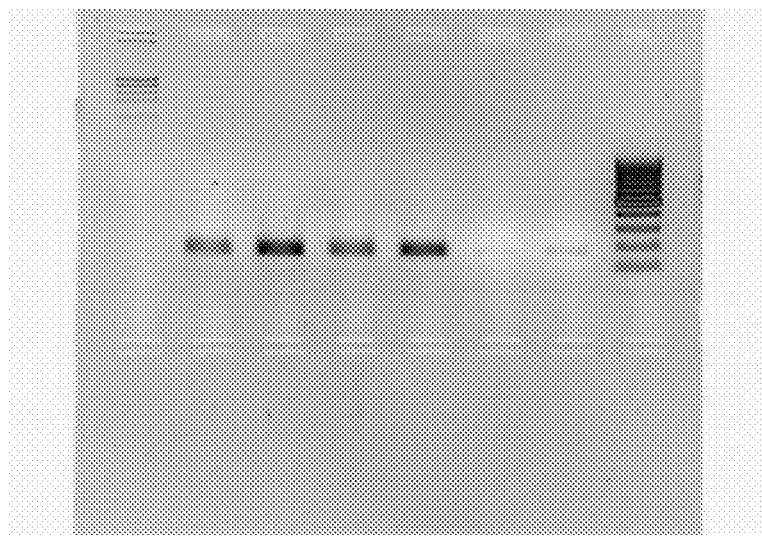
FIGS. 14A-B provides photos of agarose gels that were run with DNA fragments and markers. (A) Gel electrophoresis of olive actin (174 bp) PCR product, and DNA fragments recovered by using the freeze/thaw methods disclosed herein. Lanes 1 and 8 are DNA markers. Lanes 2, 3, 4, and 5 show 174 by olive, action DNA fragments from PCR, while, lanes 6 and 7 provide for the same olive DNA fragment which has been recovered using the freeze/thaw method disclosed herein. (B) Gel electrophoresis of DNA fragments purified by either using the freeze/thaw method of the disclosure or purified by using spin Columns from a Qiagen™ Kit, Lanes 1 and 8 are DNA markers. Lanes 3 and 4 provide for a 74 bp DNA fragment recovered from a 20-25 uL eluent using the freeze/thaw methods disclosed herein (typically >100 uL of eluent is obtained). Lanes 2 and 5 provides for a 98 bp DNA fragment recovered from 20-25 uL eluent using the freeze/thaw methods of the disclosure. Lane 6 provides for a 174 bp by DNA fragment from 15 uL of 10.8 ng/uL that was recovered from a gel using a Qiagen™ Kit (typically 10-20 uL of eluent is obtained using said kits). Lane 7 provides for a 98 bp DNA fragment from 1 uL of 11.9 ng/uL that was recovered from a gel using a Qiagen™ Kit FIG. 15 provides results of a qPCR experiment using avocado DNA templates that were recovered by using the freeze/thaw method disclosed herein.
Figure 14B:
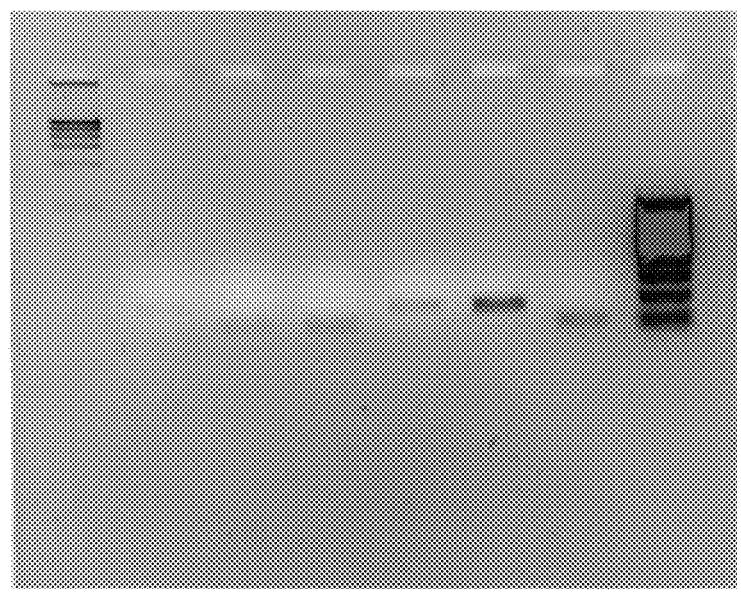

In order to find out and further to prove that freezing the gels changed the mesh (pore) size of the agar and agarose gels, different concentrations of agar or agarose were used to recover DNA, RNA, Protein or Bio-extracts from the gels. 0.8% and 3.5% agarose gels were made with TAE buffer, and sliced into 3 sections. One section was frozen at −20° C. and thawed at room temperature afterwards, another section was kept at 4° C. (not frozen). Molecular markers were loaded into the gel section and electrophoresed. Results of the electrophoresis showed that the agarose gel molecular meshes were changed after being frozen, and as result the frozen gel failed to separate DNA samples as compared with the unfrozen gel, i.e., DNA samples loaded on the frozen gel cannot be separated, by contrast, DNA sample and molecular marker were well separated on the regular unfrozen gel (see FIG. 12A-B, and FIG. 13) It was further found that agar or agarose gels have the ability to withstand about 9% volume increase without breaking the molecular meshes, and further that the agar and agarose gel meshes were permanently changed with using a freeze/thaw cycle. By contrast, an unfrozen agarose gel (1%) can be run multiple times (e.g., >5 times) and not show any changes in the mesh size.

Recovering Agar and Agarose Gel Meshes by Melting and Reforming Gels.

DNA did not separate on an agarose gel that was frozen at −20° C. and thawed at room temperature when electrophoresed. This gel was then melted using a microwave and a new gel was cast. This "new gel" was loaded with DNA samples and a marker and then ran under the same electrophoresis conditions as described above. The results with the "new gel" were the same as the unfrozen gel. Accordingly, these results demonstrate that agar and agarose molecular meshes or pore size can only be recovered by melting and re-casting the gels.

Recovering and Quantifying DNA Recovered from the Gels.

DNA recovered by using the aforementioned freeze/thaw method was quantified and qualified using a Nanodrop ND-1000 Spectrophotometer. If the recovered DNA recovered is found to have a too low concentration, the DNA can be precipitated using ethanol (see Table 1). Moreover, precipitating with ethanol also provide higher quality DNA.

TABLE 1

Concentration and quality of extracted DNA

| SAMPLE | Sample ID | Nucleic Acid Conc. | Unit | A260 | A280 | 260/280 | 260/230 |
|---|---|---|---|---|---|---|---|
| 1 | Avocado ACT | 5 | ng/μl | 0.1 | 0.072 | 1.38 | 0.6 |
| 2 | Avocado AG1 | 7.7 | ng/μl | 0.153 | 0.097 | 1.58 | 1.54 |
| 3 | Avocado AP1 | 2.8 | ng/μl | 0.057 | 0.047 | 1.21 | 0.52 |
| 4 | Avocado AP3 | 3.9 | ng/μl | 0.078 | 0.05 | 1.56 | 1.36 |
| 5 | Avocado FT | 1.2 | ng/μl | 0.024 | 0.018 | 1.32 | 0.49 |
| 6 | Avocado SEP | 2.5 | ng/μl | 0.05 | 0.034 | 1.45 | 0.32 |
| 7 | FT concentrated | 12.1 | ng/μl | 0.241 | 0.122 | 1.97 | 1.22 |

Note:
The sample ID represent PCR products from different primer pairs. Sample 7 was concentrated from sample 5 using ethanol precipitation. The concentration was increased, and the 260/280 ratio also increased to 1.97.

Comparing DNA Extracted from Using Freeze/Thawed Gels Versus DNA Extracted Using a Commercial Kit.

Figure 15:
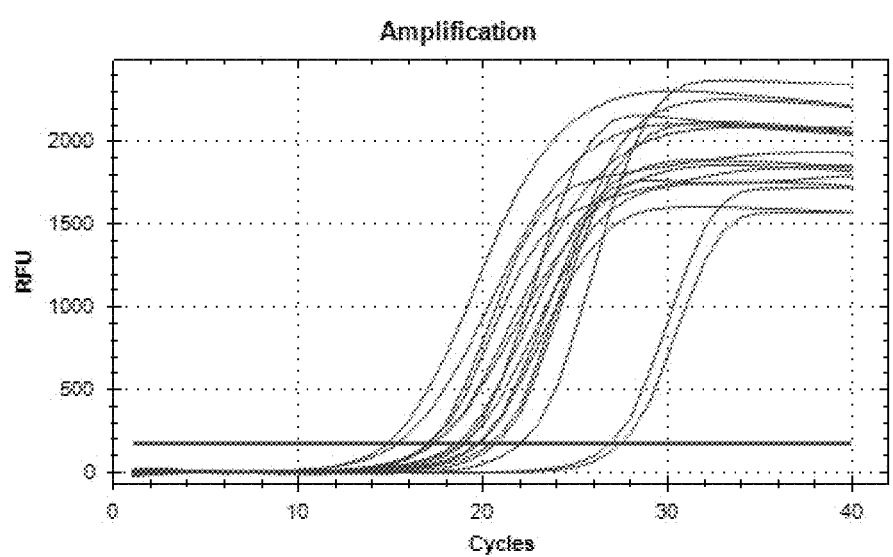

DNA recovered by using the freeze/thaw methods described herein were compared with DNA purified by using an up-dated method and kit (QIAquick Gel Extraction Kit™, catalog No. 28706). The DNA samples were run on gels, and gel slices comprising a DNA band were collected. Then gel slices were extracted either by using the freeze/thaw methods disclosed herein, or by using the commercial kit. The recovered DNA were run on an agarose gel to visualize and compare the DNA bands (see FIG. 15A-B).

Determining Whether DNA Purified by Methods Disclosed Herein was Suitable in Sensitive Assays Like qPCR.

Recovered DNA from frozen gels was used as template for qPCR to test the quality of the DNA. All results showed that the recovered DNA by using the disclosed freeze/thaw method can be used directly for QPCR without any need for further purification. (see FIG. 16, see also Table 2).

TABLE 2

CT value of QPCR from 10 ng of DNA eluted from gel using the methods of the disclosure.

| Well | Fluor | Content | Sample | Cq |
|---|---|---|---|---|
| A01 | SYBR | Unkn-1 | ACT | 19.02 |
| A02 | SYBR | Unkn-1 | ACT | 18.45 |
| B01 | SYBR | Unkn-2 | AG1 | 18.76 |
| B02 | SYBR | Unkn-2 | AG1 | 19.57 |
| C01 | SYBR | Unkn-3 | AP1 | 17.00 |
| C02 | SYBR | Unkn-3 | AP1 | 17.04 |
| D01 | SYBR | Unkn-4 | AP3 | 20.33 |
| D02 | SYBR | Unkn-4 | AP3 | 20.63 |
| E01 | SYBR | Unkn-5 | SEP | 17.26 |
| E02 | SYBR | Unkn-5 | SEP | 17.26 |
| F01 | SYBR | Unkn-6 | FT1 | 15.27 |
| F02 | SYBR | Unkn-6 | FT1 | 14.77 |

TABLE 2-continued

CT value of QPCR from 10 ng of DNA eluted from gel using the methods of the disclosure.

| Well | Fluor | Content | Sample | Cq |
|------|-------|---------|--------|-------|
| G01 | SYBR | Unkn-7 | FT2 | 19.73 |
| G02 | SYBR | Unkn-7 | FT2 | 22.01 |
| H01 | SYBR | Unkn-8 | ACT | 26.83 |
| H02 | SYBR | Unkn-8 | ACT | 27.37 |

Note:
FT2 uses 10 ng of DNA from concentrated FT 1, and unknown 8 uses cDNA as template Determining Whether DNA Purified by Freeze/Thaw Methods Disclosed Herein was Suitable for Sequencing.

DNA purified by the present method was used directly in sequencing experiments. The results showed that the recovered DNA can be used for sequencing directly. More than 10 DNA fragments extracted by the freeze/thaw methods disclosed herein were accurately sequenced.

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A gel extraction device comprising:
a multifunctional and reusable forceps, comprising:
   a left housing,
      wherein the left housing comprises a left-housing elongated arm portion connected to a left-housing rectangular shaped portion, and
      wherein the left-housing rectangular shaped portion comprises a left-housing longitudinal groove that can accommodate a first half portion of a spring and a first radius of a retractable rod assembly;
   a right housing,
      wherein the right housing comprises a right-housing elongated arm portion connected to a right-housing rectangular shaped portion, and
      wherein the right-housing rectangular shaped portion comprises a right-housing longitudinal groove that can accommodate a second half portion of the spring and a second radius of the retractable rod assembly;
   wherein the left housing and the right housing are joined together by using fastening means;
a cutting element,
   wherein the cutting element is detachably attached to the multifunctional and reusable forceps, and
   wherein the cutting element is used to cut a slice of gel from an agar or agarose gel; and
a sampler component,
   wherein the sampler component is detachably attached to the forceps, and
   wherein the sampler component in conjunction with the forceps is used to collect the gel slice.

2. The gel extraction device of claim 1, wherein the end of the elongated arm portion of the left-housing and the end of the elongated arm portion of the right-housing comprise projections that are dimensioned so as to fit into holes on the sampler component.

3. The gel extraction device of claim 1, wherein the forceps comprises:
a spring comprising a first half portion and a second half portion, wherein the left-housing longitudinal groove comprises the first half portion of the spring, wherein the right-housing longitudinal groove comprises the second half portion of the spring, and wherein the spring further comprises a plurality of hooks; and
a retractable rod assembly comprising
   a spring action projection,
   a loop that is attached to a hook of the plurality of hooks of the spring, and
   a deformable rectangular plate that can be used to engage and
disengage the spring when the spring action projection is pressed, wherein the rod can be extended by manually sliding the spring action projection forward, and wherein the rod can be retracted by using the tension of the spring by pressing down on the spring action projection; and
optionally, a small projection near the end of the plate that is attached to the spring that can fit into a small groove of the forceps housing to provide additional stability to the rod assembly.

4. The gel extraction device of claim 3, wherein the cutting element is detachably attached from the forceps when the rod is retracted by pressing down on the spring action projection.

5. The gel extraction device of claim 4, wherein the cutting element comprises
an opening that is slideably attachable to the end of rod assembly;
a cutting element housing which comprises a double edged blade, wherein the housing comprises an angular bend of greater than 90 degrees but less than 150 degrees in the middle portion of the housing; and
optionally a flat plate located at the opposite end of the cutting element.

6. The gel extraction device of claim 1, wherein the sampler component comprises:
a left sampler housing; and
a right sampler housing,
   wherein the left sampler housing and the right sampler housing can be slideably attached together, and
   wherein the left sampler housing comprises a receptacle that can accommodate the end of one of the arms of the forceps, and
   wherein the right sampler housing comprises a receptacle that can accommodate the end of the other arm of the forceps.

7. The gel extraction device of claim 6, wherein the right sampler housing has three panels:
a left panel;
a right panel,
   wherein the left panel and the right panel are of equal dimensions,
   wherein the left panel comprises a groove at the bottom of the panel, and
   wherein the right panel comprises a groove at the bottom of the panel; and
a back panel,
   wherein the back panel is shorter than the left panel and the right panel so that there is a slotted opening at the base of the back panel.

8. The gel extraction device of claim 7, wherein the left sampler housing has a bottom panel that is dimensioned to fit within the slotted opening of the back panel of the right sampler housing, and
   wherein the lateral sides of the bottom panel of the left sampler housing can slideably insert into the grooves of the left panel and the right panel of the right sampler housing.

9. The gel extraction device of claim 1, wherein the forceps is made of stainless steel; and wherein the cutting element and sampler component are made of stainless steel, plastic, or a combination thereof.

10. The gel extraction device of claim 1, wherein the cutting element and/or sampler component are disposable.

* * * * *